(12) United States Patent
Lin et al.

(10) Patent No.: US 9,063,084 B1
(45) Date of Patent: Jun. 23, 2015

(54) GAS SENSOR HAVING MICRO-PACKAGE STRUCTURE AND METHOD FOR MAKING THE SAME

(71) Applicant: LINGSEN PRECISION INDUSTRIES, LTD., Taichung (TW)

(72) Inventors: Tzu-Chih Lin, Taichung (TW); Chien-Ko Liao, Taichung (TW)

(73) Assignee: LINGSEN PRECISION INDUSTRIES, LTD., Taichung (TW)

( * ) Notice: Subject to any disclaimer, the term of this patent is extended or adjusted under 35 U.S.C. 154(b) by 24 days.

(21) Appl. No.: 14/171,378

(22) Filed: Feb. 3, 2014

(30) Foreign Application Priority Data

Dec. 27, 2013 (TW) .............................. 102148858 A

(51) Int. Cl.
*G01N 21/61* (2006.01)
*G01N 33/00* (2006.01)
*H01L 23/00* (2006.01)
*C09J 5/00* (2006.01)

(52) U.S. Cl.
CPC ............ *G01N 21/61* (2013.01); *G01N 33/0027* (2013.01); *H01L 24/85* (2013.01); *C09J 5/00* (2013.01); *G01N 2201/061* (2013.01)

(58) Field of Classification Search
CPC ........ C09J 5/00; G01N 21/3504; G01N 21/61; G01N 2201/061; G01N 33/0027; H01L 24/85
See application file for complete search history.

(56) References Cited

U.S. PATENT DOCUMENTS

| | | | |
|---|---|---|---|
| 2010/0284553 A1* | 11/2010 | Conti et al. | 381/174 |
| 2010/0314544 A1* | 12/2010 | Ouvrier-Buffet | 250/338.4 |
| 2011/0296900 A1* | 12/2011 | Thorson | 73/24.02 |

* cited by examiner

*Primary Examiner* — Mark R Gaworecki
(74) *Attorney, Agent, or Firm* — Muncy, Geissler, Olds & Lowe, P.C.

(57) ABSTRACT

A gas sensor having a micro-package structure includes a light-emitting unit, a light-receiving unit, and a signal-processing unit all deposited on a substrate, and a package body fixed to the substrate and having a chamber and a through hole. The chamber accommodates all the units and the through hole is over the substrate. Gas enters the chamber through the through hole. The light-emitting unit emits an optical signal that passes through the gas and then is received by the light-receiving unit. Then a signal-processing unit electrically connected to the light-receiving unit performs spectral analysis. Thereby, the gas sensor is advantageous for requiring low packaging costs and being compact.

11 Claims, 4 Drawing Sheets

GAS SENSOR HAVING MICRO-PACKAGE STRUCTURE AND METHOD FOR MAKING THE SAME

BACKGROUND OF THE INVENTION

1. Technical Field

The present invention relates to sensors, and more particularly to a gas sensor having a micro-package structure and a method for making the gas sensor.

2. Description of Related Art

A gas sensor works by using applicable electric signals to convert a certain gas in the air into figures for convenient monitoring and calculation. In the air, most gases are colorless and odorless, and thus undetectable by human olfaction or other human sensory functions. However, some of the gases may be dangerous when presenting in the air we breathe. Carbon monoxide, for example, when inhaled excessively by people, the people can be poisoned to faint or even die. This can be prevented and human safety can be ensured by using a gas sensor and taking appropriate ventilating measures. In another instance where the levels of carbon dioxide and oxygen in the air are to be controlled for people's good life quality, a gas sensor may be attached to an air-conditioning system so that when the level of carbon dioxide is higher than desired, the air-conditioning system can activate its air purifier to improve the air quality. It is thus evidenced that gas sensors are important to improvement in comfort and safety of human life.

FIG. 1 and FIG. 2 depict a conventional solid-electrolyte gas-sensing module 1, which comprises a substrate 2, a gas-sensing element 3 deposited on the substrate 2, and a metal cover 4 fixed to the substrate 2 and covering the gas-sensing element 3. The gas-sensing element 3 is composed of a solid electrolyte 5 of cation ($Na^+$) and a printed heater ($RuO_2$) 8 provided between a cathode (sensing electrode) 6 and an anode (counter electrode) 7. The cathode 6 is made from lithium carbonate and gold, and is connected to a first leading pin S1. The anode 7 is made of gold, and is connected to a second leading pin S2. The printed heater 8 is connected to a third leading pin (not shown) and a fourth leading pin (not shown). The gas-sensing element 3 further uses platinum wires to connect connecting pins 9 made of nickel for signal transmission. Such a gas-sensing module 1 has been rapidly developed for having advantages of high conductivity, high sensitivity, and high versatility as the gas-sensing element 3 can be modified by varying the ions generated in the material through absorption, the moving ions in the electrolyte, and the immobilized ions in the material. However, the gas-sensing element 3 is structurally complex and requires high manufacturing costs, so the price of the entire gas-detecting module 1 is consequently expansive. In addition, since a gas-sensing structure of this type is typically made as a voluminous modularized device, its use is subject to spatial abundance.

To sum up, the conventional gas-detecting module is imperfect and needs to be improved.

BRIEF SUMMARY OF THE INVENTION

The primary objective of the present invention is to provide a gas sensor having a micro-package structure and a method for making the same. The gas sensor requires less packaging costs, and is compact, thereby being more practical.

For achieving the above-mentioned objective, the gas sensor of the present invention comprises a substrate, a light-emitting unit, a light-receiving unit, a signal-processing unit, and a package body. The substrate has a light-emitting area, a light-receiving area, and a signal-processing area. The light-emitting unit is deposited in the light-emitting area and provides an optical signal. The light-receiving unit is deposited in the light-receiving area and receives the optical signal of the light-emitting unit. The signal-processing unit is deposited in the signal-processing area and electrically connected to the light-receiving unit. The package body is fixed to the substrate and has a chamber and a through hole. The chamber accommodates the light-emitting unit, the light-receiving unit, and the signal-processing unit, and the through hole is over the substrate.

Therein, the signal-processing unit is a die.

Therein, a protective layer is formed on a surface of the signal-processing unit.

Therein, the package body includes an upper lid and a lateral wall circling the upper lid and extending downward from the upper lid, and the upper lid is provided with the through hole, and defines the chamber jointly with the lateral wall.

Therein, the optical signal of the light-emitting unit is a visible light or an infrared ray, with a wavelength between 380 nm and 10000 nm.

Therein, the light-receiving unit is an infrared-ray sensor (IR Sensor).

Therein, the gas sensor further comprises a step of providing the protective layer on a surface of the signal-processing unit.

For achieving the above-mentioned objective, the present invention further provides a method for making the gas sensor, which comprises the following steps: providing the substrate and defining the light-emitting area, the light-receiving area and the signal-processing area; providing the light-emitting unit, the light-receiving unit and the signal-processing unit to the light-emitting area, the light-receiving area and the signal-processing area, respectively; providing an electrically-connecting means to the substrate and the signal-processing unit; and providing a fixedly-connecting means between the package body and the substrate.

Therein, the electrically-connecting means is a wire bonding process.

Therein, the fixedly-connecting means is gluing.

Thereby, the disclosed gas sensor is small and compact, and uses simplified manufacturing process so as to reduce the packaging costs, thereby being more practical as compared to the prior art.

For further illustrating the means and functions by which the present invention achieves the certain objectives, the following description, in conjunction with the accompanying drawings and preferred embodiments, is set forth as below to illustrate the implement, structure, features and effects of the subject matter of the present invention.

BRIEF DESCRIPTION OF THE SEVERAL VIEWS OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE INVENTION

The following preferred embodiments when read with the accompanying drawings are made to clearly exhibit the above-mentioned and other technical contents, features and effects of the present invention.

Figure 1:
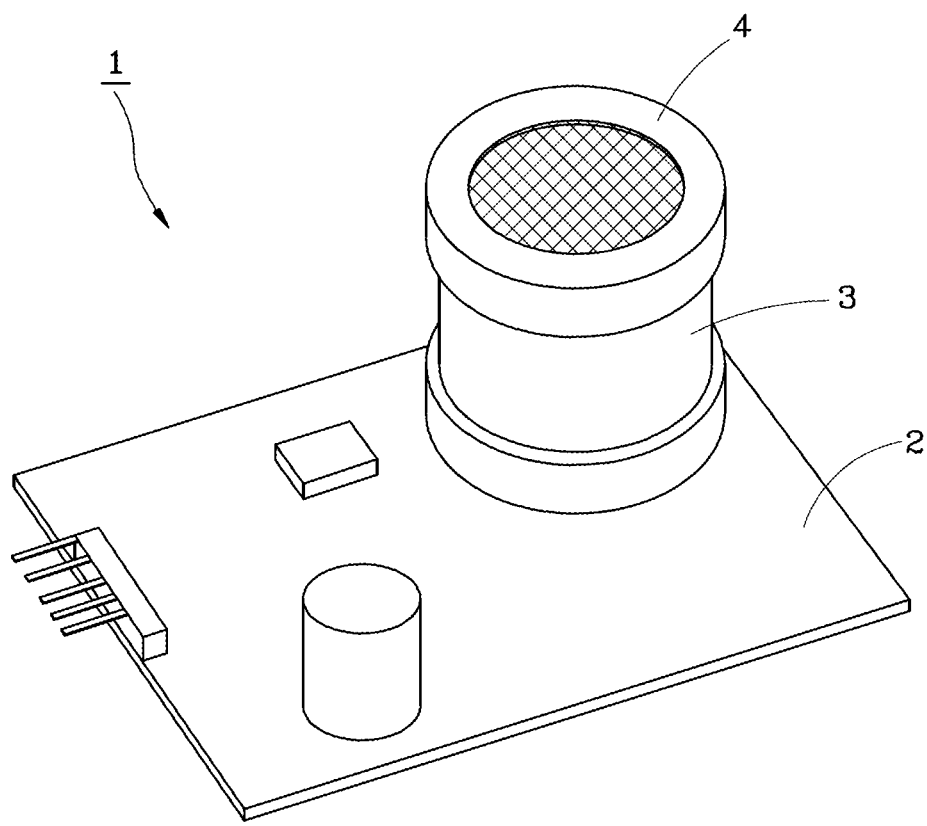
FIG. 1 is a perspective view of a conventional gas-detecting module.
Figure 2:
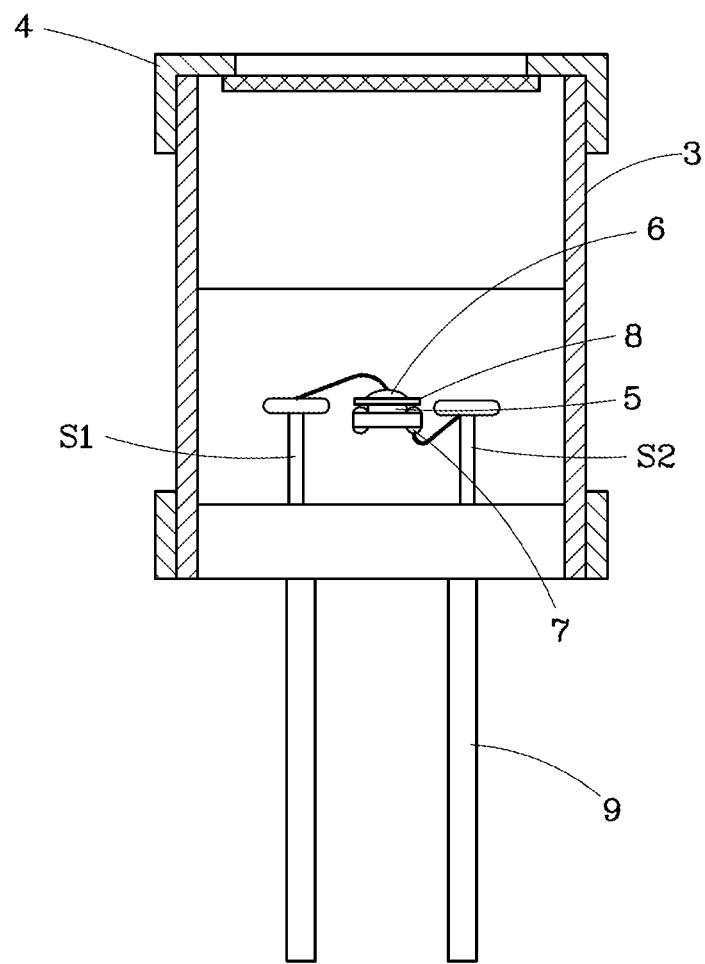
FIG. 2 is a cross-sectional view of the conventional gas-detecting module, showing the interior of its gas-sensing element.
Figure 3:
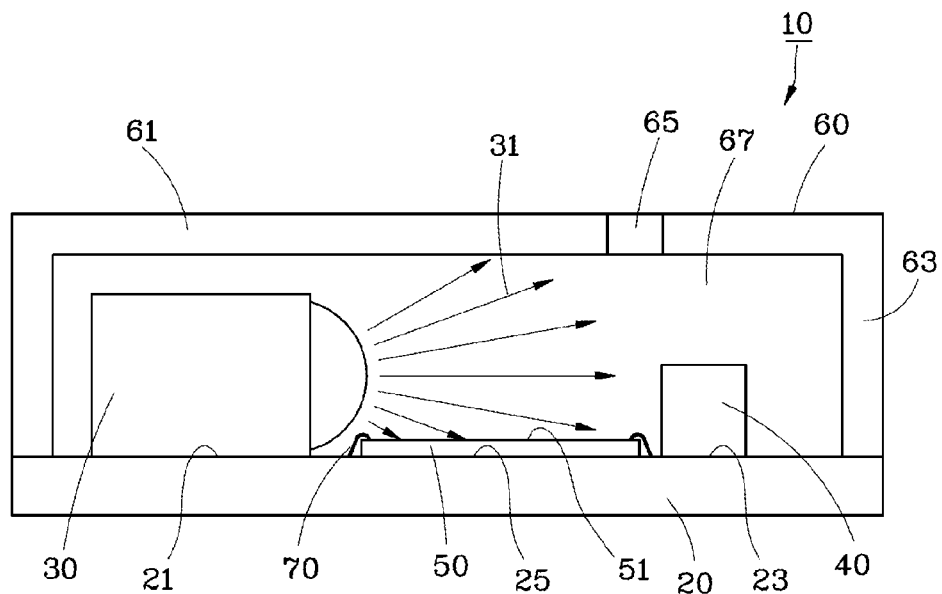
FIG. 3 is a cross-sectional view of a gas sensor according to one preferred embodiment of the present invention, showing the light-emitting unit delivering an optical signal to the light-receiving unit.
Figure 4:
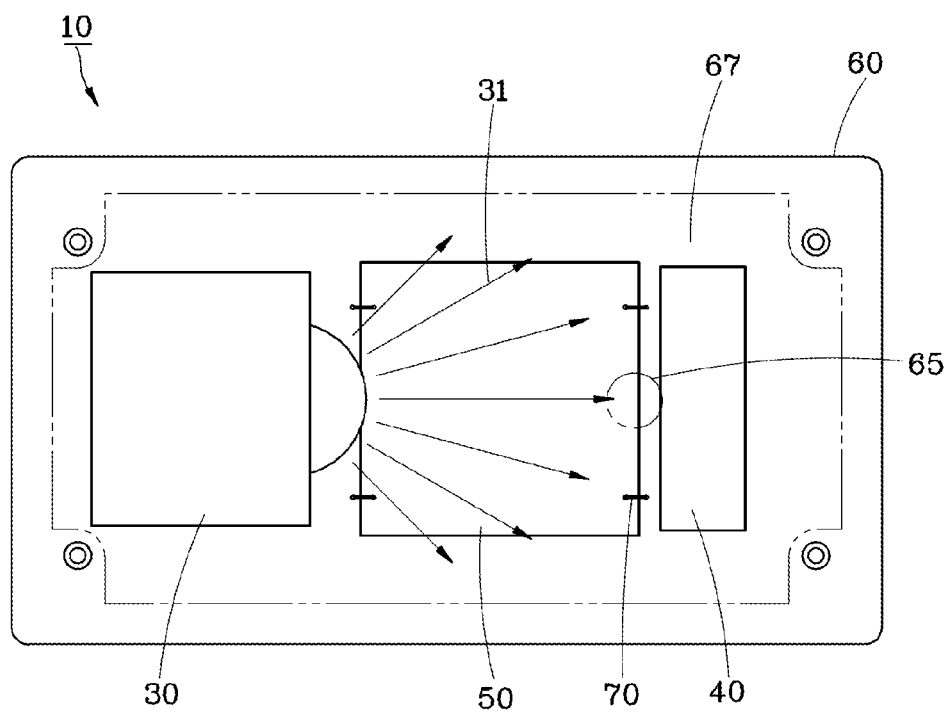
FIG. 4 is a top view of the gas sensor according to the preferred embodiment of the present invention, showing the layout of the units on the substrate.

Referring to FIG. 3 through FIG. 4, in a preferred embodiment of the present invention, a gas sensor 10 comprises a substrate 20, a light-emitting unit 30, a light-receiving unit 40, a signal-processing unit 50 and a package body 60.

The substrate 20 has a light-emitting area 21, a light-receiving area 23, and a signal-processing area 25.

The light-emitting unit 30 is deposited in the light-emitting area 21 and provides an optical signal 31. The optical signal 31 of the light-emitting unit 30 may be a visible light or an infrared ray, with a wavelength between 380 nm and 10000 nm. In the present embodiment, the optical signal 31 is an infrared ray.

The light-receiving unit 40 is deposited in the light-receiving area 23 and receives the optical signal 31 from the light-emitting unit 30. The light-receiving unit 40 in the present embodiment is an infrared-ray sensor (IR Sensor).

The signal-processing unit 50 is deposited in the signal-processing area 25 and is electrically connected to the light-receiving unit 40. In the present embodiment, the signal-processing unit 50 is realized by a die, for replacing the conventional gas-sensing element 3 and being much less voluminous. For protecting the signal-processing unit 50 in the form of the die from dust and moisture, a taping machine (not shown) is used to form a protective layer 51 over the signal-processing unit 50, so as to protect it without excessively adding its volume.

The package body 60 is fixed to the substrate 20, and includes an upper lid 61 and a lateral wall 63 circling the upper lid 61 and extending downward from the upper lid 61. The upper lid 61 has a through hole 65, and defines jointly with the lateral wall 63 a chamber 67. The chamber 67 accommodates the light-emitting unit 30, the light-receiving unit 40, and the signal-processing unit 50. The through hole 65 is formed above the substrate 20. In the present embodiment, the through hole 65 is preferably formed between the light-receiving unit 40 and the signal-processing unit 50.

Figure 5A:
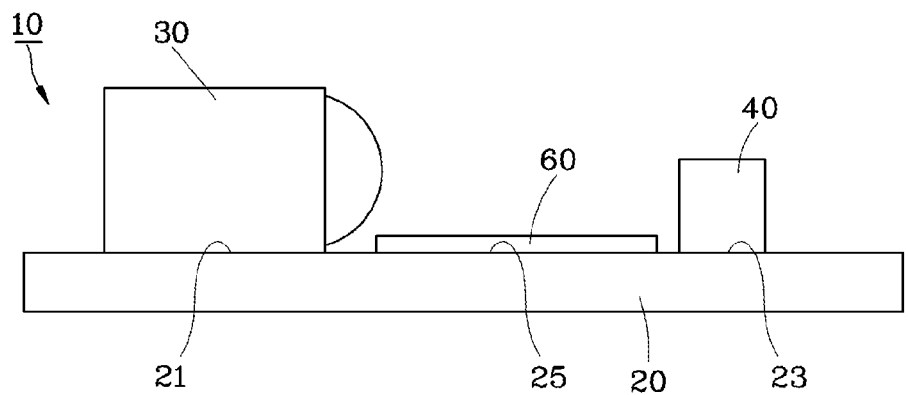
FIG. 5A through FIG. 5C illustrate the method for making the gas sensor according to another preferred embodiment of the present invention.
Figure 5B:
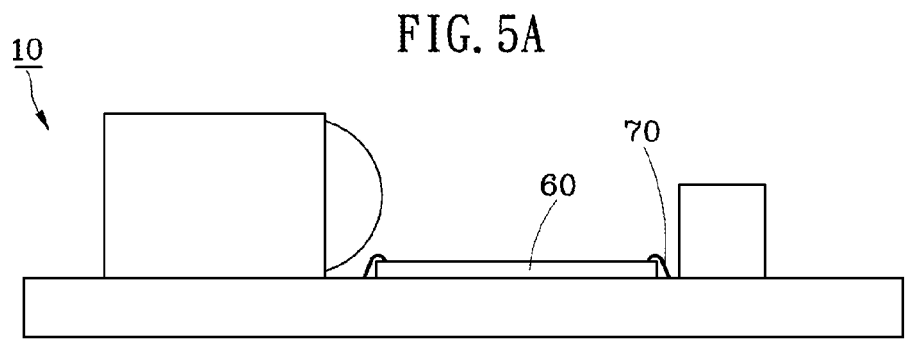
Figure 5C:
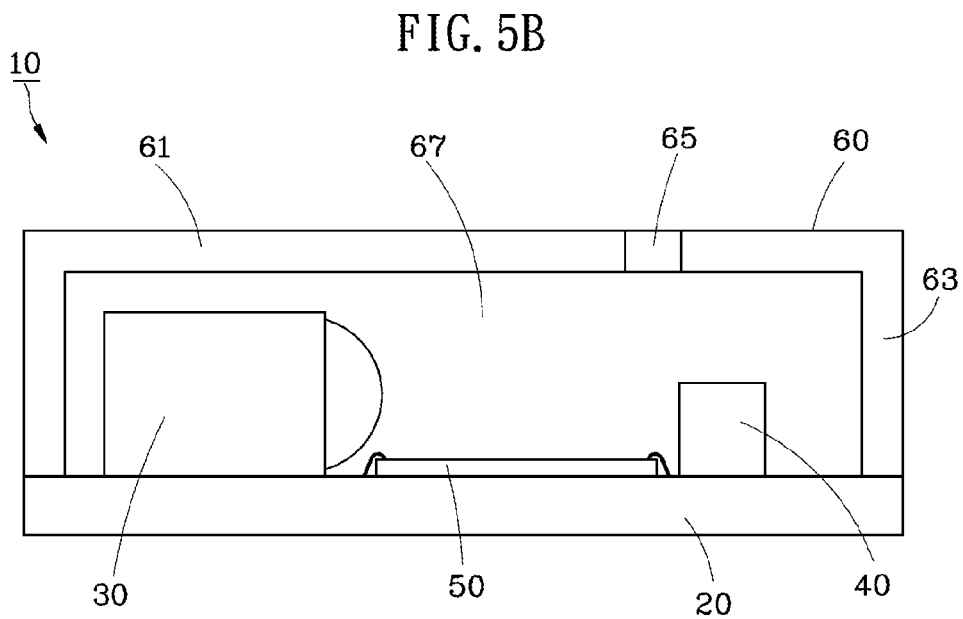

FIG. 5A through FIG. 5C illustrate a method for making the gas sensor 10 according to another preferred embodiment the present invention. The method comprises the following steps:

Step A: providing the substrate 20 and defining the light-emitting area 21, the light-receiving area 23, and the signal-processing area 25, and electrically connecting the light-emitting unit 30, the light-receiving unit 40 and the signal-processing unit 50 to the light-emitting area 21, the light-receiving area 23 and the signal-processing area 25, respectively;

Step B: providing an electrically-connecting means to the substrate 20 and the signal-processing unit 50, wherein the electrically-connecting means is using a wire bonding process to make at least one wire bond 70 connected between the substrate 20 and the signal-processing unit 50; and Step C: providing a fixedly-connecting means between the package body 60 and the substrate 20, wherein the fixedly-connecting means is gluing and in the present embodiment an adhesive use for the gluing is epoxy resin.

When the disclosed gas sensor 10 is used for gas detection, the gas to be detected flows into the chamber 67 of the package body 60 through the through hole 65 formed on the upper lid 61, and the infrared ray emitted by the light-emitting unit 30 passes through the gas to be detected and casts on the light-receiving unit 40. At the same time, the infrared ray has its wavelength affected by the gas to be detected, so the light-receiving unit 40 receiving the infrared ray works to identify the spectrum of the changed wavelength, and then passes the data to the signal-processing unit 50 for processing and analysis. At last, the data are converted into signals and output to a reading device (not shown) or a display device (not shown), so that the spectrum of the gas to be detected can be read out our displayed for a user to determine what the gas is.

In conclusion, the disclosed gas sensor 10 is small and compact, and uses simplified manufacturing process so as to reduce the packaging costs, thereby being more practical as compared to the prior art.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A gas sensor having a micro-package structure, the gas sensor comprising:
   a substrate, having a light-emitting area, a light-receiving area, and a signal-processing area;
   a light-emitting unit, being deposited in the light-emitting area and providing an optical signal;
   a light-receiving unit, being deposited in the light-receiving area and receiving the optical signal of the light-emitting unit;
   a signal-processing unit, being deposited in the signal-processing area and electrically connected to the light-receiving unit; and
   a package body, being fixed to the substrate and having a chamber and a through hole, wherein the chamber accommodates the light-emitting unit, the light-receiving unit, and the signal-processing unit, and the through hole is over the substrate.

2. The gas sensor of claim 1, wherein the signal-processing unit is a die.

3. The gas sensor of claim 2, wherein a protective layer is formed on a surface of the signal-processing unit.

4. The gas sensor of claim 1, wherein the package body includes an upper lid and a lateral wall circling the upper lid and extending downward from the upper lid, and the upper lid is provided with the through hole, and defines the chamber jointly with the lateral wall.

5. The gas sensor of claim 1, wherein the optical signal of the light-emitting unit is a visible light or an infrared ray, with a wavelength between 380 nm and 10000 nm.

6. The gas sensor of claim 1, wherein the light-receiving unit is an infrared-ray sensor.

7. A method for making the gas sensor having the micro-package structure of claim 1, the method comprising the following steps:

providing the substrate and defining the light-emitting area, the light-receiving area, and the signal-processing area;

providing the light-emitting unit, the light-receiving unit, and the signal-processing unit in the light-emitting area, the light-receiving area, and the signal-processing area, respectively;

providing an electrically-connecting means to the substrate and the signal-processing unit; and providing a fixedly-connecting means between the package body and the substrate.

8. The method of claim 7, wherein the electrically-connecting means is a wire bonding process.

9. The method of claim 7, wherein the fixedly-connecting means is gluing.

10. The method of claim 9, wherein an adhesive used for the fixedly-connecting means is epoxy resin.

11. The method of claim 7, further comprising a step of providing a protective layer on a surface of the signal-processing unit.

\* \* \* \* \*